(12) United States Patent
Herb et al.

(10) Patent No.: US 9,835,573 B2
(45) Date of Patent: Dec. 5, 2017

(54) APPARATUS AND METHOD FOR MEASURING ELECTRICAL PROPERTIES OF MATTER

(71) Applicant: Ilium Technology Inc., Medford, MA (US)

(72) Inventors: Glenn T. Herb, Weston, MA (US);
Craig A. Herb, Medford, MA (US);
Curt W. Jarva, Norwell, MA (US)

( * ) Notice: Subject to any disclaimer, the term of this patent is extended or adjusted under 35 U.S.C. 154(b) by 142 days.

(21) Appl. No.: 14/205,938

(22) Filed: Mar. 12, 2014

(65) Prior Publication Data
US 2015/0002178 A1    Jan. 1, 2015

Related U.S. Application Data

(60) Provisional application No. 61/790,668, filed on Mar. 15, 2013.

(51) Int. Cl.
*G01N 27/02* (2006.01)
*G01N 27/06* (2006.01)
*G01N 27/07* (2006.01)

(52) U.S. Cl.
CPC ........... *G01N 27/02* (2013.01); *G01N 27/028* (2013.01); *G01N 27/06* (2013.01); *G01N 27/07* (2013.01)

(58) Field of Classification Search
CPC ........ G01N 27/06–27/07; G01R 27/22; G01R 27/02; G01R 27/2623
See application file for complete search history.

(56) References Cited

U.S. PATENT DOCUMENTS 2,654,362 A    10/1953   Petersen
2,654,862 A *  10/1953   Petersen ............... 324/448
(Continued)

FOREIGN PATENT DOCUMENTS

EP    0733201        7/2000
WO    2005040780     5/2005
WO    2014/150785 A2 9/2014

OTHER PUBLICATIONS

International application No. PCT/US14/24226, International Filing Date: Mar. 12, 2014, Written Opinion of the International Preliminary Examining Authority and International Search Report dated Sep. 12, 2014.

(Continued)

*Primary Examiner* — Son Le
*Assistant Examiner* — Dustin Dickinson
(74) *Attorney, Agent, or Firm* — Burns & Levinson LLP; Jerry Cohen

(57) ABSTRACT

The present disclosure provides a method and an apparatus for measuring electrical conductivity of liquids. In one aspect, the apparatus includes a waveform generator module configured to generate a first waveform signal and to supply the first waveform signal to a sensor; a phase adjustment module configured to receive the first waveform signal from the waveform generator module and to generate a phase-shifted signal from the first waveform signal, said phase-shifted signal having a phase that is adjusted based upon expected or measured properties of the liquid and further adjusted to eliminate phase error induced inaccuracies in the measurement; and a signal combination module configured to receive a return signal from the sensor and the phase-shifted signal from the phase adjustment module and to sum the return signal and the phase-shifted signal to produce an (Continued)

adjusted return signal containing information associated with the electrical property of the liquid.

40 Claims, 5 Drawing Sheets

(56) References Cited

U.S. PATENT DOCUMENTS

| | | | |
|---|---|---|---|
| 3,457,501 A * | 7/1969 | Ingram | 324/448 |
| 4,585,996 A | 4/1986 | Luce | |
| 4,701,713 A * | 10/1987 | Eaton | G01N 27/06 |
| | | | 324/439 |
| 4,713,347 A | 12/1987 | Mitchell et al. | |
| 5,138,264 A | 8/1992 | Seki | |
| 5,225,783 A | 7/1993 | Suzuki | |
| 5,266,899 A | 11/1993 | Bull et al. | |
| 5,343,758 A * | 9/1994 | Ingrain et al. | 73/861.02 |
| 5,414,368 A | 5/1995 | Ogawa et al. | |
| 5,455,513 A * | 10/1995 | Brown et al. | 324/445 |
| 5,459,406 A * | 10/1995 | Louge | G01F 1/64 |
| | | | 324/688 |
| 5,481,197 A | 1/1996 | Sanders et al. | |
| 5,508,610 A * | 4/1996 | Feeney | G01N 27/023 |
| | | | 324/227 |
| 5,872,454 A * | 2/1999 | West | G01N 27/06 |
| | | | 324/439 |
| 5,874,832 A | 2/1999 | Gabelich | |
| 5,943,908 A | 8/1999 | Innes et al. | |
| 8,054,085 B2 * | 11/2011 | Johansen et al. | 324/548 |
| 8,127,603 B2 * | 3/2012 | Nagata | 73/290 R |
| 2003/0141882 A1 | 7/2003 | Zou et al. | |
| 2010/0188111 A1 | 7/2010 | Fougere | |
| 2011/0193573 A1 * | 8/2011 | De Boer | G01B 7/023 |
| | | | 324/686 |
| 2012/0056632 A1 * | 3/2012 | Dhirani | G01N 27/4473 |
| | | | 324/692 |
| 2012/0068723 A1 | 3/2012 | Sullivan | |
| 2013/0035606 A1 * | 2/2013 | Wichner | A61B 5/7203 |
| | | | 600/546 |

OTHER PUBLICATIONS

Supplementary Partial European Search Report dated Dec. 2, 2016, Application No. EP 14 76 9551, published May 7, 2000, parent PCT/US14/24226, priority date Mar. 12, 2014.
Extended European Search Report in corresponding European Application No. 14769551.4 dated Mar. 28, 2017, (16 Pages).

* cited by examiner

APPARATUS AND METHOD FOR MEASURING ELECTRICAL PROPERTIES OF MATTER

RELATED APPLICATION

This application claims priority to U.S. Provisional Application No. 61/790,668, filed on Mar. 15, 2013, the entire contents of which are incorporated herein by reference, for all purposes, as if stated/shown at length herein.

TECHNICAL FIELD

The present disclosure relates to an apparatus and a method for measuring the electrical conductivity, dielectric constant, and related properties of matter and includes apparatus and a method for precisely measuring the electrical conductivity of liquids with conductivities ranging from extremely low (~$10^{-15}$ S/cm) to moderately high (~$10^{-3}$ S/cm). (S/cm=Siemens per centimeter).

RELATED ART

Measuring very low conductivity in liquids (<1 nS/cm) (nano-Siemens per cm) has historically posed a problem for instrumentation. In addition to the obvious issues with resistive leakage paths, liquids have a tendency to polarize under an electric field and can form double layers at electrode interfaces that can mask the bulk of the sample from the measurement field. To compensate for this polarization, most conductivity measurements of liquids are done using an alternating polarity (AC) waveform. The frequency of this waveform is chosen to be fast enough so that no appreciable field masking due to double layer polarization occurs in the sample being measured before the polarity of the measuring field switches. Typical frequencies for these AC measurements can range from much greater than 10 KHz for aqueous systems to less than 1 Hz for some non-aqueous systems.

Adding to the measurement problems is that when using an AC measurement waveform, parasitic capacitance shunting the sample being measured can cause large out-of-phase return signals. When the conductivity being measured is very low, these out-of-phase currents can be orders of magnitude larger than the in-phase return signal of interest. Not only can these out-of-phase signals overload input amplifier stages, but since the value of shunt capacitance is usually a strong function of the dielectric constant of the liquid being measured, for a general purpose liquid conductivity meter, the shunt capacitance itself can vary by greater than 50 to 1 depending on the sample being measured. Some prior art systems have worked to compensate for the external wire capacitance, but have assumed that the parasitic capacitance shunting the sample is only a function of measurement cell geometry and is a fixed value. See, for example, U.S. Pat. No. 7,550,979 to Zhou et al., entitled SYSTEM AND METHOD FOR MEASURING CONDUCTIVITY OF FLUID and U.S. Pat. No. 6,232,786 to Barnett, entitled APPARATUS AND METHOD FOR MEASURING CONDUCTIVITY. Other prior art systems have tried to minimize this shunting capacitance at the expense of reduced cell constant and/or limiting the types of liquids that can be measured. See, for example, U.S. Pat. No. 8,552,750 to Fougere, entitled APPARATUS AND METHOD FOR THE MEASUREMENT OF ELECTRICAL CONDUCTIVITY AND DIELECTRIC CONSTANT OF HIGH IMPEDANCE FLUIDS.

It is usually desirable to use a sine wave drive to sense the conductivity since this allows for extremely narrow band discrimination of the return signal, which aids in eliminating noise from harmonics, near drive frequency cross-talk, and other unwanted interfering signals. See, for example, U.S. Pat. No. 6,232,786 to Barnett, entitled APPARATUS AND METHOD FOR MEASURING CONDUCTIVITY. This can work well for systems where the out-of-phase return signals are manageable, but as the ratio of out-of-phase to in-phase return components becomes very large, errors tend to increase rapidly, dramatically reducing the accuracy of the measurement.

Liquid conductivity meters using sine wave drive have historically tried to deal with this large out-of-phase return component by attempting to subtract out a specific amount of quadrature phase signal from the return signal (see, for example, Operator Manual for Model 627 Conductivity Meter, which was commercially available from Scientifica, Princeton, N.J. and referenced in U.S. Pat. No. 6,265,883). However, because the out-of-phase return signal, and therefore the compensating subtraction signal, can be orders of magnitude larger than the in-phase return signal of interest, extremely small phase errors in the compensating quadrature phase subtraction signal can cause relatively large measurement accuracy errors.

Non-sine wave (for example square wave) drive signals are also used to measure conductivity in liquid systems. See, for example, U.S. Pat. No. 6,265,883 to Clark, entitled APPARATUS AND METHOD FOR COMBINING MEASUREMENT OF ELECTRICAL PROPERTIES AND DEPTH OF A FLUID, and U.S. Pat. No. 4,683,435 to Blades, entitled CIRCUIT FOR COMPENSATING NON-LINEARITIES IN ELECTROLYTE CONDUCTIVITY MEASUREMENT SYSTEM. With sample systems that have extremely low conductivities and substantial shunt capacitance, using a non-sine wave drive can isolate the capacitive return signal and remove some of the difficulty of dealing with the large accuracy errors that can occur when attempting to resolve the very small phase angles involved in separating out the in-phase return signal component. When using a non-sine wave drive, much of the signal to noise improvement gained by the use of narrow band drive signals can be lost. In addition, the frequency used is no longer just a function of what is required to prevent double layer formation at the electrodes. The frequency must be kept low enough for the current spike at the waveform transition edges caused by the parasitic shunt capacitance to decay away before a measurement can be taken. This can limit the frequencies that can be used on some systems.

With an instrument capable of determining the conductivity and dielectric constant of fluids with conductivities ranging from about 1 fS/cm (femto-Siemens per centimeter) (e.g., 1,4-dioxane or toluene) up to about 1 mS/cm (milli-Siemens per centimeter) (e.g., 5 mM aqueous KCl solution) and dielectric constants ranging from 1.8 (e.g., pentane or hexane) to almost 200 (e.g., n-methylacetamide or n-methylformamide), it is also desirable to have probes for which the cell constant (defined as A/L, the Area to gap-Length ratio) does not change over the entire range of fluid parameters that might be encountered. Due to fringing of the electric field at the edges of the electrodes, the effective area of the electrodes is always larger than would be calculated from the geometric area based on the electrode dimensions. Since the extent of the fringing of the electric field is a function of the sample properties, it is desirable to use a cell design for which the effect of the fringing on the cell constant is small and for which the change in effective cell constant is negligible for all samples ranging from the smallest to the largest possible dielectric constant or conductivity. Such a cell allows the cell constant to be determined at any one point in the covered range, rather than requiring the use of conductivity standards very close to the value for the unknown sample and requiring multiple calibration constants even for a modest range of conductivities and dielectric constants. Although guarded, parallel plate cells with both fixed and adjustable cell constants have been described (Dikarev, B. N. et al., Dielectric Materials, Measurements and Applications Conference Publication No. 473, © 2000, "Design Features of the Test Cells for Conductivity Measurement in Dielectric Liquids"), most conductivity cells currently available are not guarded and require multiple calibration fluids to define multiple calibration constants, which must be stored in the meter. Although cumbersome, this method is possible in the higher (e.g. aqueous) conductivity ranges (>10 uS/cm (micro-Siemens per centimeter)) since there are several well-known standards available in this region. However, in the entire region below 1 uS/cm there are currently no reliable calibration fluids available. This is particularly problematic since the dielectric constants in this region cover a much larger range of 2 to 80. Clearly fully guarded cells would be an improvement for liquids in this range. Because cells with high A/L ratios are required in this lower conductivity region, concentric cylinders are often the geometry of choice since they are more compact and the electrode alignment is less error prone than parallel plates. However, we are not aware of concentric cylinder probes for which the signal electrode is fully guarded by guard electrodes placed at both ends of it.

Prior art probes also maintain the concentricity of the cylinders with supports at both ends of the cylinders, supports at multiple points along the cylinder (see, for example, Operator Manual for Model 627 Conductivity Meter, commercially available from Scientifica, Princeton, N.J.), or by screwing the outer cylinder to a flat stop (see, for example U.S. Pat. No. 8,552,750 to Fougere, entitled APPARATUS AND METHOD FOR THE MEASUREMENT OF ELECTRICAL CONDUCTIVITY AND DIELECTRIC CONSTANT OF HIGH IMPEDANCE FLUIDS). Two end support and multiple point support methods are difficult to disassemble for cleaning or are difficult to clean assembled without compromising the reproducibility of the cell constant. The method of screwing the outer cylinder to a flat stop allows disassembly, but is prone to loss of reproducibility of the cell constant following each disassembly/reassembly cycle as well as with extended use and wear. Except as otherwise stated herein, "liquids" or "fluids" as used herein include single or mixed chemical species, single or multi-phase organic or inorganic chemicals or biologics, and including e.g. suspensions, dispersions, emulsions, liquids with gas bubbles (i.e. liquid as a continuous phase). The liquid to be tested can be static or dynamic (flowing and/or turbulent).

SUMMARY

The present disclosure provides (at assembly, sub-assembly, and component, hardware/software levels) an apparatus, a system, and a method that enable measurement of electrical properties of liquids/fluids in a way to compensate for the problems encountered in the prior art.

The system of the present disclosure is generally a measurement apparatus connected to a probe, sample holding device, or sensor. The measurement apparatus generally comprises a signal-driving-unit that is capable of exciting the sample in contact with the probe or sample holding device and a return-signal-processing-unit. The signal-driving-unit further comprises a programmable waveform generator that is capable of producing waveforms of various wave shapes, amplitudes, frequencies (including DC), and phase. The return-signal-processing-unit further comprises one or more amplifiers, filters whose characteristics can be dynamically changed, signal modification elements capable of adding to or subtracting from the signal, and other signal processing components.

The programmable waveform generator within the signal-driving-unit may produce wave shapes such as sine, square, triangle, etc., in single or multiple forms (e.g. square wave pulsing superimposed on a sine, square, triangle etc. waveform). When the signal-driving-unit is producing a sine wave, the system of the present disclosure uses the return-signal-processing-unit to detect the out-of-phase component of the return signal and dynamically compensates for it by subtracting out an appropriate amount of out-of-phase signal at the input amplifier. This ensures that the in-phase component of the return signal can be amplified without clipping due to the out-of-phase signal. Since any phase error in the compensation signal can cause undesirable degradation in accuracy, the system of the present disclosure is constructed to self calibrate the phase of its compensation signal at all used frequencies and, if necessary, gains.

The system can then determine the conductivity of the sample from the in-phase component of the return signal, and as an added benefit, can determine the system/sample shunt capacitance from its monitoring of the out-of-phase return signal and the required level of compensation signal. This capacitance information can be used to calculate other sample properties such as dielectric constant. It should also be noted that in systems with high conductivity and low shunt capacitance (e.g. high conductivity fluids being measured with probes using low Area/gap-Length ratios) where the in-phase return signal is much larger than the out-of-phase (quadrature) return signal, the system of the present disclosure can be used to find the dielectric constant with higher accuracy by having the compensation section subtract out the in-phase component allowing for larger amplification of the quadrature return signal.

The system of the present disclosure also dynamically determines what kind of a waveform is optimal for measuring the conductivity of the sample that is presented. It can, for example, make (or be adjusted to make) a first estimate of the conductivity and shunt capacitance using a sine wave drive, and based on that first estimate, determine the best frequency and wave shape to use to measure the sample. During on-going measurements, it continues to check for the optimum frequency and drive wave shape. It does this either as an ongoing check using its current measurement parameters, or by switching in and out of its current measurement parameters to an alternate set of parameters that are more optimal for sensing capacitance and other "setting determining" functions. This allows it to track slowly changing sample characteristics as well as dramatic sample changes. If the system determines that a non-sine wave drive is more appropriate due to the range of conductivity and shunt capacitance present, it uses its measured values of conductance and shunt capacitance to choose the best wave shape, and frequency for the measured sample in order to maximize accuracy and performance.

After the wave shape and frequency have been chosen, the system constantly adjusts the amplitude of the drive waveform and the gain of the input amplifier chain to optimize the measured return signal and its signal to noise characteristics.

The external signal and drive wires connected to the conductivity measurement cell or probe are both independently shielded and the shields are connected so as to electrically guard the return signal in such a way that there is effectively no capacitive load or shunt on the signal return wire and little or no resistive leakage between the signal return wire and the guard. This allows for a wide range of cable lengths to be used without causing any effect to the measurement circuitry and is an improvement over the prior art where cable and connection capacitance caused major issues (see, for example, U.S. Pat. No. 7,550,979 to Zhou et al., entitled SYSTEM AND METHOD FOR MEASURING CONDUCTIVITY OF FLUID and U.S. Pat. No. 6,232,786 to Barnett, entitled APPARATUS AND METHOD FOR MEASURING CONDUCTIVITY, the entire contents of which are incorporated herein by reference in their entirety for all purposes as though set out/shown at length herein.

Both before and after the system has processed the return signal and digitally separated out the in-phase and out-of-phase return signals, it applies various adaptive filters to the signal to further improve signal to noise.

The present disclosure provides adaptive compensation and wave shape, which allows for a very wide range of conductivity measurements with auto ranging capabilities; the wide range of shunt capacitance that can be tolerated by the disclosed apparatus allows for measurement cells ranging from small to very large A/L (Area/gap-Length) ratios, i.e. the probe's cell constant; adaptive filters provide more stable readings at the extremes of the system's ranges; and self calibration, including the self calibration of the phase of the compensating out-of-phase signal over all used gains and frequencies, dramatically increases accuracy of measurements over an extremely large range of conductivities, dielectric constants and probe cell constants.

The instrument described in this disclosure is capable of determining the conductivity and dielectric constant of fluids with conductivities ranging from about 1 fS/cm (e.g., 1,4-dioxane or toluene) up to about 1 mS/cm (e.g., 5 mM aqueous KCl solution) and dielectric constants ranging from 1.8 (e.g., pentane or hexane) to almost 200 (e.g., n-methylacetamide or n-methylformamide). A short list of example liquids that fall within this range are given in Table 1 below:

TABLE 1

Examples of liquids which are all within the measurement range of the disclosed apparatus

| Solvent | Conductivity (S/cm) | Relative permittivity (dielectric constant) |
| --- | --- | --- |
| 1,4-Dioxane | 5.0E−15 | 2.2 |
| 1,2-Dichloroethane | 40.0E−12 | 10.4 |
| Nitrobenzene | 200.0E−12 | 34.8 |
| Acetonitrile | 600.0E−12 | 35.9 |
| Methanol | 1.5E−09 | 32.7 |
| Dimethyl sulfoxide | 2.0E−09 | 46.5 |
| Acetone | 5.0E−09 | 20.6 |
| Nitromethane | 5.0E−09 | 36.7 |
| Water | 60.0E−09 | 78.4 |
| N-Methylformamide | 800.0E−09 | 182.4 |
| 1 mM Aq. KCl solution | 147.0E−06 | 78.4[3] |

Notes:
(1) All values at 25 degrees Centigrade
(2) Unless otherwise noted, data is from "Electrochemistry in Nonaqueous Solutions", Kosuke Izutsu, Wiley-VCH, 2009
[3]From "Physical Chemistry", Third Edition, Daniels & Alberty, John Wiley & Sons, 1966

Because of the wide range of values that can be measured by this instrument, it is also desirable to have probes for which the cell constant (defined as A/L, the Area to gap-Length ratio) does not change over the entire range of fluid parameters that might be encountered. The current disclosure also provides a probe design utilizing a fully guarded signal electrode as well as incorporating a taper mechanism to accurately maintain the concentricity between the outer cylinder electrode and the inner cylinder electrodes. The taper design further enables the ability to easily remove the outer electrode to facilitate cleaning while providing a robust method of ensuring that the cell constant remains unchanged even after many removal/re-attachment cycles.

BRIEF DESCRIPTION OF THE DRAWINGS

The various features and advantages of the present disclosure may be more readily understood with reference to the following detailed description taken in conjunction with the accompanying drawings, wherein like reference numerals designate like structural elements, and in which.

DETAILED DESCRIPTION

The present disclosure provides a method for measuring the electrical conductivity, dielectric constant, and related properties of liquids and an apparatus that implements said method. The present disclosure also provides a guarded probe for use with the measurement apparatus.

Figure 1:
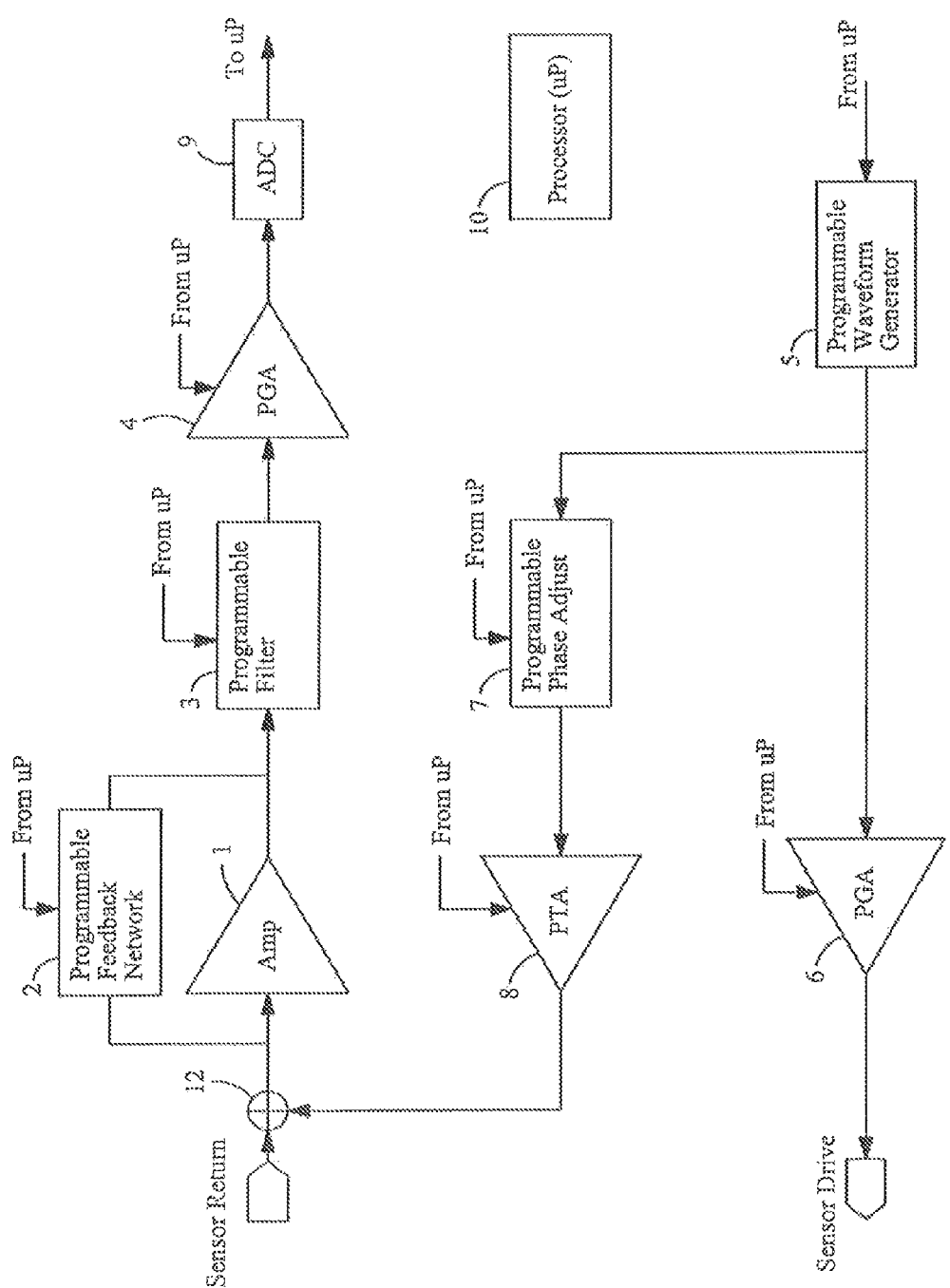
FIG. 1 illustrates a schematic circuit diagram according to an embodiment of the present disclosure.

FIG. 1 shows a schematic circuit diagram according to an embodiment of the present disclosure, the circuit comprising major components indicated below as being coupled to a liquid sample sensor (cell or probe) and to a processor. The processor 10 can be of standard form, e.g., a Texas Instruments TMS320F2808 microprocessor controller for transmitting manual and/or programmed instructions to the circuit components and storing and managing data obtained. It is programmed to implement the process steps described below.

The return-signal-processing-unit's amplifiers and filters whose characteristics can be dynamically changed are schematically represented by amplifier 1, feedback network 2, programmable filter section 3, and programmable voltage gain amplifier 4 as shown in FIG. 1. The sensor return signal is connected to the summing junction 12 of an amplifier 1 −+ which can be implemented with a component such as Analog Devices, Inc. AD8627−+, which is connected to perform as a transimpedance amplifier. The feedback network 2 around the amplifier 1 is controlled by the processor 10 and in one embodiment can vary the gain of the amplifier 1 from about 10,000 V/A to about 100 million V/A. The output of the transimpedance amplifier 1 is connected to a programmable filter section 3 −+ which can be implemented with components such as a Maxim MAX7424 and MAX7405 connected so that the processor can control both and select which one is being used+.

The processor 10 controls the characteristics of the filter 3 to optimize the band-pass to produce the best wave shape and signal to noise performance for a given expected return signal. For example, in one embodiment, if the expected return signal is a low frequency sine wave, the programmable filter 3 is adjusted to provide a linear phase characteristic with a high frequency cut off, which is a precise small multiple of the expected frequency. That insures that the return sine wave is passed on with a well-known calculated phase shift and that the noise bandwidth of the return signal is minimized.

As another example, if the expected return waveform is a square wave, the filter's high frequency cut off is set much higher than the fundamental frequency of the square wave so as not to distort the edges of the waveform and the characteristics of the filter are changed from a linear phase type filter to a fast roll off elliptical type filter since sine wave phase shift is no longer an important issue.

The programmable filter 3 is connected to a programmable voltage gain amplifier 4, which in one embodiment has gains ranging from 1× to 100× +which can be implemented with a component such as a Linear Technology LTC6912+. The processor 10 controls the gain of this amplifier to make the processed return signal as large as possible without causing signal clipping or distortion. The output of the programmable amplifier 4 is connected to an analog to digital converter (ADC) 9 +which can be implemented with a component such as an ADC integrated into the microprocessor+, which in turn is connected to the processor 10.

In one embodiment, the processor 10 controls the ADC sampling rate to be an exact multiple of the stimulus frequency (regardless of wave shape) and controls its detection algorithm to be in phase with the output stimulus signal. The synchronous nature of the detector is able to measure the in-phase and out-of-phase components of the return signal in a sine stimulus drive and is also able to automatically adjust for the polarity reversals of a square wave stimulus signal. The synchronous nature of the detector results in a very narrow band filter for noise reduction. Both before and after the system has processed the return signal and digitally separated out the in-phase and out-of-phase return signals, it applies various adaptive filters to the signal to further improve signal to noise.

The signal-driving-unit in accordance with one embodiment is schematically represented by the programmable waveform generator 5 and programmable voltage gain amplifier 6 as shown in FIG. 1. To control the sensor's drive electrode, the processor 10 sets the programmable waveform generator 5 +which can be implemented with a component such as an Analog Devices AD9837+ to a waveform type and frequency that is appropriate for the sample being measured. This waveform generator 5 is not only used to change frequency based on the sensed characteristics of the sample being measured, but also used to change the wave shape based on range and type of characteristic being measured. For example, for a sample with a very low value of conductivity (e.g., 100 fS/cm) and a relatively high system shunt capacitance (e.g., 750 pF), it might be best to measure the conductivity with a square wave at 1 Hz. The optimum frequency for the square wave, however, is a function of both the speed at which the double layer forms at the electrodes and the system shunt capacitance. It is therefore necessary to periodically check the value of the system's shunt capacitance as well as its conductivity to insure that the frequency range is correct. While a 1 Hz square wave may be optimum for the conductivity measurement, the capacitance may be best measured with a sine wave at 100 Hz. In this example, the processor 10 can periodically switch the drive from the 1 Hz square wave to a 100 Hz sine wave, make the appropriate capacitance measurement, set the new conductivity drive parameters if necessary, and then switch back to those conductivity drive parameters. Waveforms other than sine and square can of course be generated and used as appropriate, for example, triangle waves, trapezoidal waves, modified trapezoid waves (e.g., truncated sine wave), compound waves (e.g., superimposition of sine wave, square wave, etc.), and other arbitrarily shaped waveforms. This ability allows the system to be used to measure arbitrary liquids and liquids with changing characteristics, for example, titration experiments or production mixing measurements.

The waveform generator 5 is connected to a programmable voltage gain amplifier 6. The processor 10 adjusts the gain of this amplifier 6 to put enough drive amplitude on the sensor's drive electrode to maximize signal to noise without causing return signal clipping or over stressing the sample being measured. The output of this amplifier 6 is connected to the sensor's drive electrode.

Figure 2A:
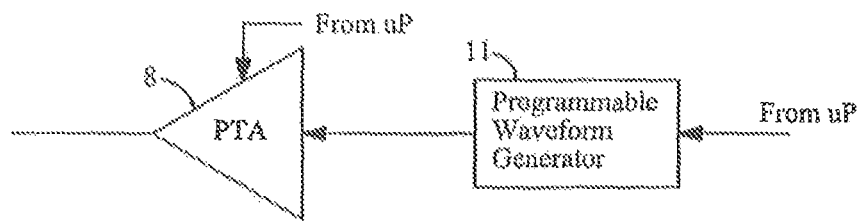
FIGS. 2A and 2B illustrate a schematic circuit diagram according to an alternate embodiment of the programmable phase adjustment function of the present disclosure.
Figure 2B:
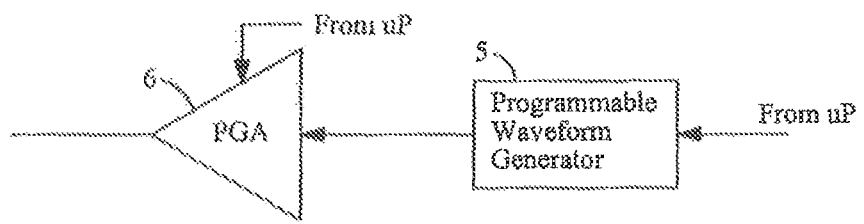

To implement the signal modification element, which is capable of adding to or subtracting from the sensor return signal, the waveform generator 5 is also connected to a programmable phase adjuster 7. This function can also be accomplished with two separate programmable waveform generators 5 and] 11 that are set to be a programmed phase apart from each other (see FIG. 2). The processor 10 adjusts the phase of this path (FIG. 1 item 7 or FIG. 2 item 11) so that it is equal to and opposite in sign from (i.e., 180 degrees out of phase with) the detected out-of-phase component of the return signal. This phase adjusted signal is connected to a programmable gain transconductance amplifier 8 the output of which is connected to the summing junction 12 of the transimpedance amplifier 1.

The processor 10 controls the gain of the transconductance amplifier 8 to convert its input voltage waveform to the appropriate amplitude current waveform to subtract out most of the incoming out-of-phase component. This reduces or eliminates the out-of-phase component the input transimpedance amplifier sees and can prevent signal clipping in systems with very low conductivities and high shunt capacitance. In such cases, the return signal component from the shunt capacitance (out-of-phase) can be orders of magnitude larger than the component from the conductivity (in-phase). Because of this, small phase errors in the compensating subtracted current can cause large measurement errors as these phase errors project some of the compensation signal onto the return signal's in-phase component.

Figure 3:
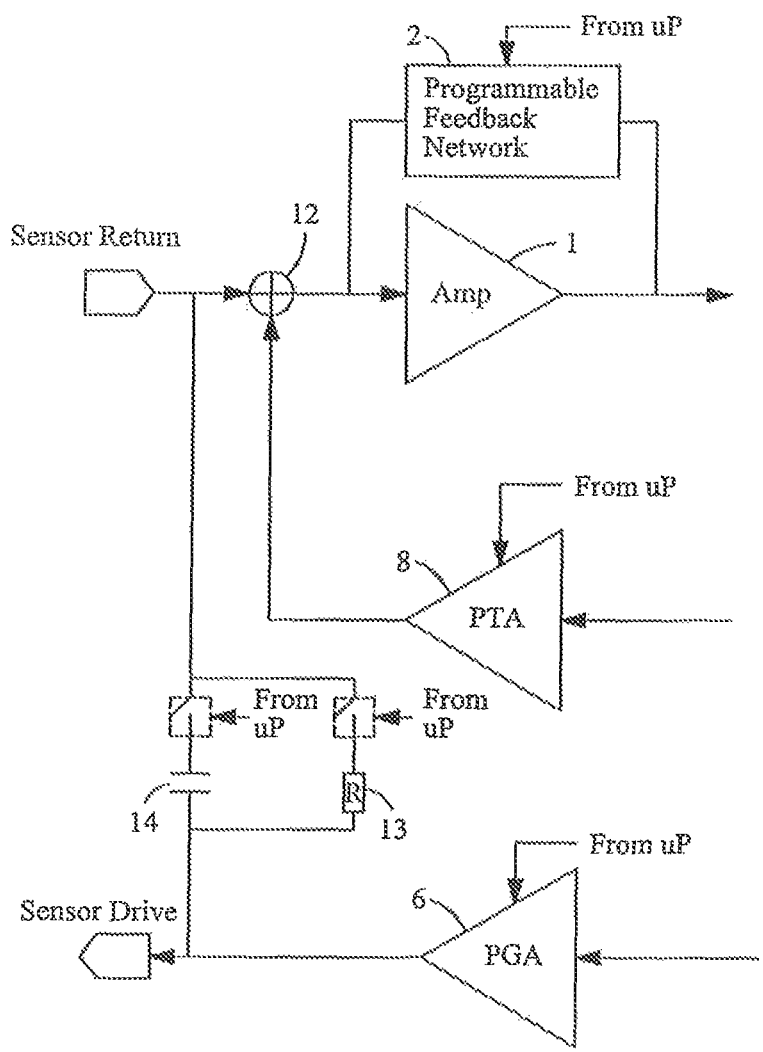
FIG. 3 illustrates a schematic circuit diagram showing an embodiment of the calibration function of the present disclosure.

The apparatus of the present disclosure can internally calibrate the phase of this compensating signal. In one embodiment, (referring to FIGS. 1 & 3) as part of the calibration cycle, the sensor is disconnected from the signal return input and a sine wave of known phase is introduced into the input transimpedance amplifier 1 via the programmable transconductance amplifier 8. The phase of the signal being measured at the ADC 9 is then used to determine the system's phase error through that path. Next, the transconductance amplifier gain is set to zero and an internal calibration precision resistor 13 is connected between the output of the drive amplifier 6 and the signal return input. A sine wave signal is then applied to the output sensor drive line and the phase of the return signal is measured at the ADC 9.

The processor 10 now knows the internal phase errors in all of the signal paths and uses this information to properly set the phase adjustments used in the compensating signal as well as any algorithmic correction. This process is repeated for all used drive frequencies and, if necessary, gains.

In another embodiment, as part of the calibration cycle, the sensor is disconnected from the signal return input and an internal calibration capacitor 14 is connected between the output of the sensor drive amplifier 6 and the signal return input. A sine wave signal is then applied to the output sensor drive line. The capacitive connection causes a 90-degree out-of-phase signal to appear on the input of the transimpedance amplifier 1. The transconductance amplifier 8 gain is set so as to minimize the out-of-phase component at the output of the transimpedance amplifier 1 as in normal operation. In an ideal system, this should provide an in-phase component of zero amplitude, but in a real system, there is a residual in-phase component.

The waveform driving the transconductance amplifier 8 is then swept through a phase range, with the ADC synchronous detection algorithm synchronized to each phase. When the detected in-phase amplitude crosses from a negative to positive value, the optimal phase is found by interpolating between the closest negative and positive reading phase values. The system uses this information to properly set the phase adjustments used in the compensating signal as well as any further algorithmic correction. The algorithmic correction is used by the system's processor to further correct the phase induced error beyond the resolution capabilities of the hardware programmable phase adjuster. This process is repeated for all used drive frequencies and, if necessary, gains.

The absolute values of the various input adjustable gain blocks are also calibrated using an on-board precision resistor 13. In addition, any scaling requirements between sine, square, and any other used waveform are also calibrated.

To aid in minimizing unwanted system capacitance, the external signal return and drive wires connected to the conductivity measurement cell, sensor, or probe are both independently shielded and the shields are connected so as to electrically guard the return signal in such a way that there is effectively no capacitive load or shunt on the signal return wire and little or no resistive leakage between the signal return wire and the guard. This allows for a wide range of cable lengths to be used without causing any effect to the measurement circuitry and is an improvement over the prior art where cable and connection capacitance caused major issues. With an instrument capable of determining the conductivity and dielectric constant of fluids with conductivities ranging from about 1 fS/cm (e.g., 1,4-dioxane or toluene) up to about 1 mS/cm (e.g., 5 mM aqueous KCl solution) and dielectric constants ranging from 1.8 (e.g., pentane or hexane) to almost 200 (e.g., n-methylacetamide or n-methylformamide), it is also desirable to have probes for which the cell constant (defined as A/L, the Area to gap-Length ratio) does not change over the entire range of fluid parameters that might be encountered.

Figure 4A:
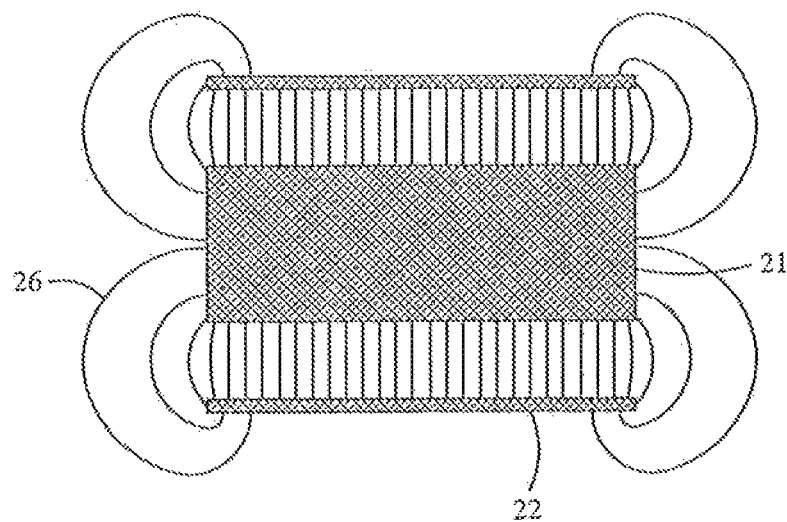
FIGS. 4A and 4B illustrate schematic diagrams of an unguarded and fully guarded concentric cylinder conductivity cell.

The probe in one embodiment comprises a concentric cylinder design. The probe can include guarded, unguarded, or only partially guarded signal electrodes. As can be seen in FIG. 4A, the field lines 26 between the outer cylinder electrode 22 and the signal electrode 21, although uniform in the center of the probe, fringe at the ends of the signal electrode. This fringing causes the effective cell constant (A/L) to be larger than that calculated from the geometry of the probe. The extent of this fringing is a function of the physical properties of the sample under test (e.g., dielectric constant), thus causing the effective cell constant to vary significantly over the wide range of sample properties measurable with the system disclosed.

Figure 4B:
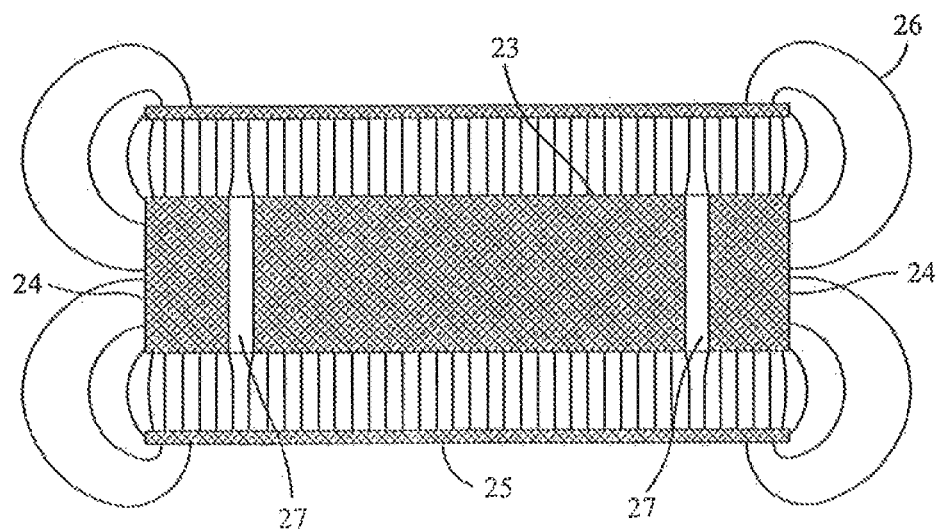

In one embodiment, the probe employs a fully guarded signal electrode. As can be seen in FIG. 4B, the guard electrodes 24, which are kept at essentially the same potential as the signal electrode 23, cause the field lines 26 between the outer cylinder electrode 25 and the signal electrode 23 to remain essentially uniform over substantially the entire length of the signal electrode. Moreover, with sufficiently thin insulator rings 27 between the signal electrode and the guard electrodes, the variation of the slight non-uniformity near this area causes a negligible change in the cell constant over the full range of liquid properties encountered.

Figure 5A:
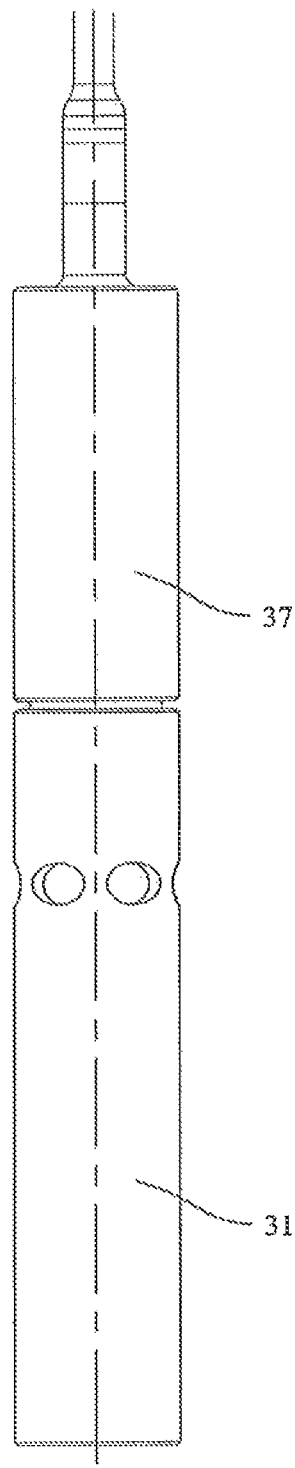
FIGS. 5A and 5B illustrate a cross section diagram of a fully guarded concentric cylinder conductivity cell of the present disclosure.
Figure 5B:
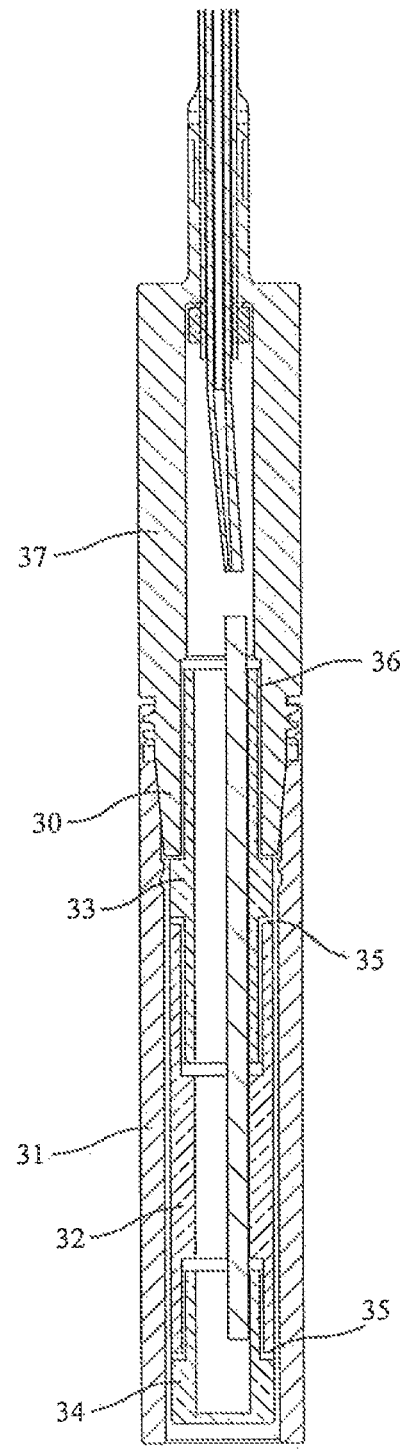

The probe in one embodiment also uses a taper to accurately maintain the concentricity between the outer cylinder electrode and the inner cylinder electrodes. FIG. 5A shows an external view of this probe and FIG. 5B shows a sectional view of this probe. The use of a taper 30 to maintain the concentricity of the inner cylinder assembly and outer electrode 31 eliminates the need for any mechanical support at the far end or any other point along the cylinders, allowing for ease of fluid flow and clean-out. It also enables the ability to easily remove the outer electrode to facilitate cleaning while providing a robust method of ensuring that the cell constant will remain unchanged even after many removal/re-attachment cycles.

The inner electrode assembly comprises a central (signal) electrode 32 separated from an upper guard electrode 33 and a lower guard electrode 34 by thin, insulating bushings 35. An insulator 36 separates the upper guard electrode 33 from the tapered hub 37 that makes contact with the outer (drive) cylindrical electrode 31. By using insulators between the signal and guard electrodes that are very thin compared to the length of the signal electrode, the effective cell constant can be kept very close to the geometric cell constant for all sample liquids. If the width of the insulators are on the order of the gap-length between the two concentric electrodes, or more preferably equal to or less than the gap length, it is possible to keep the change in cell constant below 0.1% as the dielectric constant changes from 1.8 to 200. Both guard electrodes shield the signal electrode from external noise signals, and the upper guard electrode effectively eliminates any leakage current from the drive electrode. This design results in a probe for the measurement of conductivity that is well shielded from external electrical noise and has a cell constant that is effectively independent of the sample material being measured. Cabling and electrical connections have been partially removed from FIG. 5B for clarity.

Hereafter, apparatus and method for measuring electrical properties of matter in accordance with the present disclosure are described in further detail.

AGC Corrections for Operating Environment

The above described instrument rapidly measures conductivity in a wide range of fluid specimens having a large range of base conductance and dielectric properties that require automatic gain control (AGC) correction. As a result of the large range of intended measurement targets, the instrument must encompass a very large dynamic range of gain in order to be able to digitize input signals large enough to perform calculations and small enough to not saturate amplifiers and/or the analog to digital converter. Furthermore, the dielectric property of a given specimen presents itself as a bulk capacitance in parallel with the resistive conductivity measurement.

Along with needing to operate over the described large signal dynamic range, the instrument also operates over a range of frequencies, typically from DC or near DC to several thousand Hz. This means that any fluid capacitance presents as an input current proportional to frequency and with a 90 degree phase shift in addition to the resistive measurement current. The AGC deals with these properties using several gain adjustment devices, programmable filters, capacitive current subtraction devices, variable frequency and phase waveform direct digital synthesis (DDS) devices, and an analog to digital converter (ADC).

In a typical measurement task, the AGC provides an output stimulus driving voltage (e.g., sine or square wave) at a frequency in some range. The resulting resistive and capacitive (quadrature) currents are input to a variable gain transimpedance (current to voltage) amplifier. In order to not saturate the transimpedance amplifier with quadrature signal proportional to specimen capacitance and stimulus frequency, the AGC is configured to calculate and apply a quadrature current 180 degrees out of phase with the specimen capacitive current at an amount needed to nearly cancel it. In the case of square wave stimulus this quadrature current is not present.

Following the transimpedance amplifier, the signal is conditioned with out of band analog low pass filters (to filter any high frequency noise) followed by a variable bandwidth programmable filter (5 pole Bessel for sine wave signals, or 8 pole butterworth for square wave signals). The filters are followed by a programmable gain amplifier (PGA) and finally the analog to digital converter. The dynamic range of the AGC is a function of the available output and input gains. The output stimulus is generated by a fixed gain DOS of adjustable frequency and phase waveform (e.g., sine or square) followed by a 14 bit gain adjustment digital to analog converter (DAC). The DAC thus has an adjustment resolution of 1/16383. The transimpedance amplifier accepting the resulting input current has selectable gain ranges of nominally, e.g., 10K V/A, 1 M V/A, 10 M V/A, and 100 M V/A.

In the case of sine wave stimulus, a current pump circuit using, for example, a transconductance amplifier can provide an adjustable quadrature subtraction current via a second DOS (adjustable frequency and phase) and a second 14 bit DAC channel. Following the transimpedance amplifier and filters, the PGA has programmable nominal gain selections from 1V/V to 100 V/V. The ADC is a 12 bit converter having a resolution of 1/4095. Gain adjustment range thus is from 1 M V/A*1/16383 to 1000 M V/A or (20 log(16838*100*10))=164 dB. In addition to the gain range, the ADC of course has a range over which signals are large enough for computation and small enough to insure no saturation. If this range is something like 50 ADC counts to 3500 ADC counts then the dynamic range is further increased by another 37 dB for a total of 201 dB.

The AGC is configured to find the appropriate signal gain and quadrature subtraction over this enormous range to achieve optimal signal levels for conductivity and dielectric constant measurement. Further, the system has the capability to synchronize the ADC process with the stimulus waveform. This synchronization allows the ADC process to provide an output that is proportional to an in-phase representation (with respect to stimulus voltage phase) of input current and in the case of sine wave mode, an output that is proportional to the quadrature (90 degrees phase shifted) current resulting from specimen capacitance.

For instance, since the ADC process knows that it is in phase with the stimulus voltage and it has a fixed number of data acquisition events per stimulus period, if it sums the readings for the first half of the period and subtracts the readings for the second half, a result that is proportional to an in phase sine wave and independent of any 90 degree phase shifted sine wave can be achieved. Similarly, the amount of quadrature signal independent of any in-phase signal can be calculated by summing and subtracting the appropriate samples during the period. A second feature is that, to achieve higher results resolutions, the ADC process can be commanded to accumulate multiple periods of stimulus frequency before reporting a new result for computation.

Ideal AGC Operation

The AGC can function, as necessary, in an iterative process that may take many instances to achieve the final settings. Since new information required for the AGC takes some time to be acquired, the AGC typically performs an operation and returns control to other processes while new ADC data is acquired in the background. To allow iterative operation and to know at what state in the process it is and what the history of adjustment has been it keeps some static flags and values that indicate whether the AGC has been already in process and some information about the effects of what has been previously done. If this is the first iteration of a new AGC process, these flags and values are initialized and the ADC accumulation count is setup. Higher accumulation numbers provide higher ADC signal output resolution and noise immunity at the expense of time of acquisition, so this value can range from 1 for lower frequencies to many periods for higher frequencies and faster periods. The AGC identifies to external processes via a globally accessible flag that it is active. On each iteration of the AGC, it waits for the ADC to indicate it has acquired a new set of data (typically this acquisition has been occurring in the background while some other process has been running and so is available to the AGC when it is invoked). The AGC first checks for AGC saturation. If there is saturation, but only either high or low level but not both, a routine to null input offset is called since any DC level not at ½ the ADC input voltage range could result in such a symptom even if the overall gain is satisfactory. This process will only occur once and on further iterations of the AGO any saturation is considered equally. If saturation is seen the PGA setting is examined and if greater than 1V/V is lowered one step (the gains are arranged in 1, 2, 5, 10, 20, 50, and 100 V/V steps) and control returns to external processes. On the next AGO iteration if the saturation is still seen and the PGA has reached 1 V/V then the transimpedance amplifier gain is examined and if higher than 1 MV/A is lowered a decade on each AGC iteration until it reaches 1 MV/A. If after lowering the input gains a subsequent AGC iteration is still seeing saturation the output signal level DAC is lowered by a factor of 2. If sine wave mode is active the quadrature subtraction current DAC is also lowered by a factor of 2. If the AGC cannot achieve a viable signal after iterations of this process it will indicate to other processes that it is limited low and end.

Once a signal that is in range has been acquired (i.e., saturation is not indicated by the ADC), any input DC offset is nulled (as it is likely that a previous AGO iteration has changed a gain) and a reading indicating the peak to peak input as measured by the ADC is made. If the peak to peak value is larger than some limit (too close to saturation) it is deemed that the gain needs to be lowered. First, if the drive voltage output DAC is greater than 1000 it is halved. If this is not the case and the PGA is greater than 1 V/V, it is lowered one level. If the PGA is at 1 V/V then the transimpedance gain is lowered. After each change the AGC returns to external processes.

If the peak to peak signal is less than the lower limit of an acceptable range then it is deemed that the gain needs to be increased. If the value is less than half of the upper limit of the range, the output voltage drive DAC is increased by a factor of 1.5. If the value is greater than ½ of the upper limit of the acceptable range, but below the lower limit of the range then the DAC is increased by a factor equal to 0.95 times the upper limit divided by the peak to peak value. Any increases are of course limited to the full scale value of the DAC. Furthermore, since the quadrature subtraction current will also need to increase by the same multiplicative factor, any change is limited to the amount that would saturate the quadrature subtraction current output DAC as well. In square wave mode the quadrature DAC is not an issue and is held at 0. Any time a change is made to an output DAC in sine wave mode the next iteration of the AGC will run the quadrature current subtraction process which measures the amount of quadrature input from the ADC and adjusts the subtraction current output DAC accordingly.

Once the output DAC has been increased as high as it can be, if the peak to peak input is still too low, the input gains need to be increased. If the peak to peak signal is less than $\frac{1}{10}$ of the acceptable range upper limit and the transimpedance gain is at 1 MV/A, the gain is increased to 10 MV/A. If on a subsequent AGC iteration, the peak to peak value is still less than $\frac{1}{10}$ of the upper acceptable limit or the PGA gain is 5V/V or greater the transimpedance gain is increased to 100 MV/A. If the peak to peak level was greater than $\frac{2}{10}$ of the upper acceptable range limit then the PGA gain is lowered two increments. If the value was greater than $\frac{1}{10}$ but less than $\frac{2}{10}$ of the upper limit the PGA gain is only lowered one increment. After transimpedance gain adjustments, if the peak to peak signal is still too low, then the PGA gain is to be increased. The peak to peak value is scaled up according to how much a PGA setting increment would increase gain (either 2× or 2.5×) to calculate what the next expected peak to peak reading will be. If this value is greater than the upper limit of the acceptable range then the output DAC voltage is lowered in concurrence with the PGA increase to adjust the net gain lower by an amount expected to keep the peak to peak value in the acceptable range. In the case where the expected peak to peak increase will not exceed the upper limit of the acceptable change, the PGA gain is increased one level without any output DAC adjustments. Once the maximum value of the PGA (100 V/V) is reached, if the input signal is still too low, then a globally accessible flag is set that indicates the AGC is at maximum, unless the quadrature current subtraction output DAC is at full scale in which case a flag indicating that the AGC gain is capacitance limited is set.

Possible Complications and Resolution

The above algorithm works well with ideal signals. However, in actual measurement circumstances there can be complications. One such complication is the presence of non-synchronous noise signals which can range from high frequency switching noise to 60 Hz pickup. Measurement noise is exacerbated by the presence of capacitance in the target sample. Capacitance can provide an impedance path for noise current that is orders of magnitude less than the sample resistance. For instance a capacitance of 100 pF has an impedance at 18 Hz of 88 MOhm which could be in parallel with a resistive measurement of 10's of GOhm. One notable effect of non-synchronous noise is that the measured resulting ADC signal level is a function of input gain (i.e. increasing the PGA gain increases the noise level accordingly), but decoupled from output gain (i.e. changing the output DAC level changes the signal level but not the noise level). The AGC infers the presence of noise by detecting ADC saturation in cases where it expected no such saturation due to a change. For instance in the case as described in the previous section where the PGA is to be increased, but the increase would be expected to produce an ADC output that is too large, the increase is accompanied by a reduction in the output voltage DAC to bring the expected signal back into range. This of course doesn't work in the case where a large part of the signal is noise and not signal, since the PGA increase increases the noise level, but the DAC adjustment does not lower it. So in the case where the AGC sees ADC saturation, in cases where it isn't expecting it, it lowers the acceptable ADC range and it limits PGA increases to those which won't require a concurrent reduction in output DAC voltage. Other considerations come into effect regarding the noise composition. The sine and square wave modes of operation each have a programmable filter associated with their signal paths. In the sine mode case the filter breakpoint is set to be the output signal frequency divided by 0.456 which along with filtering provides a precise 90 degree phase shift that is easily accounted for in the ADC acquisition process. At 18 Hz and lower this breakpoint results in very good noise discrimination at 60 Hz and above. Of course at higher signal frequencies the ability to attenuate 60 Hz noise is reduced or nonexistent. Square mode cannot tolerate a filter breakpoint so close to the operating frequency because of the resulting signal distortion as the filter decays from the square mode step changes. Because of this the square mode filter is set to be at the operating frequency divided by 0.14. With this setting no appreciable 60 Hz discrimination occurs until the stimulus frequency is at or below 4.5 Hz.

Another complication is that square wave mode never runs in isolation, but is instead accompanied by interludes of sine wave mode so that system capacitance can be measured. This is useful for instance in distinguishing open probe/empty probe conditions (very high resistance and low capacitance) from very high impedance samples, where square mode would normally be in effect (this open probe/empty probe detection could optionally be reported to the user). It is also useful for determining, due to capacitance, what a good square wave frequency would be in order to discriminate against noise. For higher capacitances it is desirable to run at lower frequencies where the 8 pole butterworth filter can attenuate 60 Hz pickup as described above. Because of the differing noise environments as well as the presence of quadrature current in sine mode, the two modes generally operate at largely different AGC settings. To accommodate this, the AGC runs independently in both modes generating an optimal set of settings for each. These values are memorized in holding registers so that upon switching from one mode to the other the proper values can be restored. Each mode gets stable signals where the AGC does not have to be continually adjusting (and throwing step changes into the input circuitry), however initial step changes where circuitry common to both modes such as output voltage level, quadrature current subtraction setting, and transimpedance gain that must be adjusted, do exist. This requires a waiting period after each mode switch to allow the associated filters to settle. The result is that after this initial waiting period on a mode change, the AGC does not have further adjustments to make.

For the purpose of better describing and defining the present disclosure, it is noted that terms of degree (e.g., "substantially," "about," and the like) may be used in the specification and/or in the claims. Such terms of degree are utilized herein to represent the inherent degree of uncertainty that may be attributed to any quantitative comparison, value, measurement, and/or other representation. The terms of degree may also be utilized herein to represent the degree by which a quantitative representation may vary (e.g., and not as a limit, ±10%) from a stated reference without resulting in a change in the basic function of the subject matter at issue.

It is to be understood that the above-described embodiments are merely illustrative of some of the many specific embodiments that represent applications of the principles discussed above. Clearly, numerous and other arrangements can be readily devised by those skilled in the art without departing from the scope of the claims.

What is claimed is:

1. An apparatus for measuring an electrical property of a liquid, the apparatus comprising:
   a waveform generator module configured to generate a first waveform signal and to supply the first waveform signal to a sensor;
   a phase adjustment module configured to receive the first waveform signal from the waveform generator module and to dynamically generate a phase-shifted signal from the first waveform signal, said phase-shifted signal having a phase or amplitude that is adjusted in response to expected or measured properties of the liquid and further adjusted to compensate for apparatus hardware phase error induced inaccuracies in the measurement; and
   a signal combination module configured to receive a return signal from the sensor and the phase-shifted signal from the phase adjustment module and to sum the return signal and the phase-shifted signal to produce an adjusted return signal containing information associated with the electrical property of the liquid.

2. The apparatus of claim 1, further comprising a filter module configured to receive the adjusted return signal from the signal combination module and to frequency filter the adjusted return signal.

3. The apparatus of claim 2, therein the filter module comprises a programmable amplifier and a programmable filter component.

4. The apparatus of claim 3, wherein the programmable amplifier comprises a programmable feedback network for varying a gain of the programmable amplifier from about 10,000 V/A to about 100,000,000 V/A.

5. The apparatus of claim 3, wherein the filter module further comprises a programmable voltage gain amplifier and an analog-digital converter.

6. The apparatus of claim 1, wherein the return signal from the sensor comprises art in-phase component and an out-of-phase component, and the phase-shifted signal comprises an inverse of the out-of-phase component of the return signal.

7. The apparatus of claim 1, wherein the first waveform signal comprises a sine wave and the waveform generator module is further configured to generate a square wave, each of the first waveform signal and the generated square wave being dynamically determined the apparatus as optimized for the liquid sample measurement to be acquired.

8. The apparatus of claim 7, wherein the return signal is a sine wave, and the filter module is configured to perform a high frequency cutoff on the adjusted return signal.

9. The apparatus of claim 7, wherein the return signal is a square wave, and the filter module is configured to perform a high frequency cutoff on the adjusted return signal.

10. The apparatus of claim 7, wherein the waveform generator module is configured to periodically alternate the first waveform signal between sine and square waves.

11. The apparatus of claim 1, further comprising a programmable voltage gain amplifier coupled to the waveform generator module for maximizing a signal to noise ratio of the first waveform signal.

12. The apparatus of claim 1, further comprising a programmable transconductance amplifier coupled to the phase adjustment module.

13. The apparatus of claim 1, further comprising the sensor.

14. The apparatus of claim 13, wherein the sensor comprises:
   an electrode section comprising inner and outer cylindrical electrodes;
   a base portion upon which one of the inner and outer cylindrical electrodes is mounted, the base portion having a first tapering section, and the other of the inner and outer cylindrical electrodes having a second tapering section configured such that the first and second tapering sections engage with each other to maintain precise concentricity between the inner and outer cylindrical electrodes; and
   a fastener configured to hold the first and second tapering sections.

15. The apparatus of claim 14, wherein the fastener comprises threads on the electrode section and the base portion.

16. The apparatus of claim 1, wherein the first generated waveform is selected based on properties of the liquid being analyzed.

17. A method of measuring an electrical property of a liquid, the method comprising:
   applying to a liquid sample a first imposed waveform signal;
   receiving a return signal from the liquid sample;
   generating a phase-shifted signal from the first imposed waveform signal by adjusting a phase of the first imposed waveform signal based upon expected or measured properties of the liquid and further adjusting the phase to eliminate apparatus hardware phase error induced inaccuracies; and
   adding the phase-shifted signal to the return signal to provide an adjusted return signal containing information associated with the electrical property of the liquid.

18. The method of claim 17, further comprising frequency filtering the adjusted return signal to obtain a final signal containing said information associated with the electrical property of the liquid.

19. The method of claim 17, wherein generating the phase-shifted signal comprises adjusting the phase and an amplitude of the first imposed waveform signal based upon the expected or measured properties of the liquid and further adjusting the phase and the amplitude to eliminate apparatus hardware phase error induced inaccuracies.

20. The method of claim 17, wherein, the return signal comprises an in-phase component and an out-of-phase component, and the phase-shifted signal is substantially an inverse of the out-of-phase component of the return signal.

21. The method of claim 17, wherein the first imposed waveform signal comprises a sine wave being dynamically determined by the apparatus as optimal for the liquid sample measurement to be acquired.

22. The method of claim 21, further comprising applying a square wave to the liquid sample before or after applying the sine wave to the liquid sample.

23. The method of claim 22, further comprising performing a high frequency cutoff on the adjusted return signal, wherein the cutoff frequency is sufficiently high so as to maintain edges of the return signal.

24. The method of claim 22, further comprising alternating the first imposed waveform signal between the sine wave and square wave.

25. The method of claim 21, further comprising performing a high frequency cutoff on the adjusted return signal.

26. A non-transitory computer readable storage medium having instructions stored therein, the instructions being executable by a computer apparatus and, when executed, causing a test apparatus to perform a method for measuring an electrical property of a liquid, the method comprising:
applying to a liquid sample a first imposed waveform signal;
receiving a return signal from the liquid sample;
generating a phase-shifted signal from the first imposed waveform signal by adjusting a phase of the first imposed waveform signal based upon expected or measured properties of the liquid and further adjusting the phase to eliminate test apparatus hardware phase error induced inaccuracies; and
adding the phase-shifted signal to the return signal to provide an adjusted return signal containing information associated with the electrical property of the liquid.

27. The non-transitory computer readable storage medium of claim 26, wherein the method further comprises frequency filtering the adjusted return signal to obtain a final signal containing said information associated with the electrical property of the liquid.

28. The non-transitory computer readable storage medium of claim 26, wherein generating the phase-shifted signal comprises adjusting the phase and an amplitude of the first imposed waveform signal based upon the expected or measured properties of the liquid and further adjusting the phase and the amplitude to eliminate apparatus hardware phase error induced inaccuracies.

29. The non-transitory computer readable storage medium of claim 26, wherein, the return signal comprises an in-phase component and an out-of-phase component, and the phase-shifted signal is substantially an inverse of the out-of-phase component of the return signal.

30. The non-transitory computer readable storage medium of claim 26, wherein the first imposed waveform signal comprises a sine wave being dynamically determined by the apparatus as optimal for the liquid sample measurement to be acquired.

31. The non-transitory computer readable storage medium of claim 30, wherein the method further comprises applying a square wave to the liquid sample before or after applying the sine wave to the liquid sample.

32. The non-transitory computer readable storage medium of claim 31, wherein the method further comprises performing a high frequency cutoff on the adjusted return signal, wherein the cutoff frequency is sufficiently high so as to maintain edges of the return signal.

33. The non-transitory computer readable storage medium of claim 31, wherein the method further comprises alternating the first imposed waveform signal between the sine wave and square wave.

34. The no computer readable storage medium of claim 30, wherein the method further comprises performing a high frequency cutoff on the adjusted return signal.

35. A probe for measurement of electrical properties of a liquid comprising:
an outer cylindrical electrode;
an inner cylindrical electrode concentric with the outer electrode; and
two cylindrical guard electrodes respectively disposed adjacent an end of the inner signal electrode and electrically isolated from the inner signal electrode by insulators having respective widths less than or equal to the gap between the concentric outer and inner signal electrodes and thinner than the respective lengths of the outer and inner signal electrodes, wherein the guard electrodes are configured to cause electric field lines between the outer cylinder electrode and the inner signal electrode to remain uniform over substantially an entire length of the inner signal electrode and reduce electric field fringing at the edges of the signal electrode, such that a cell constant change of the probe is negligible with respect to a range of the electrical properties of the liquid, whereby the electrical properties comprise liquid conductivity, and the range is between about 1 fS/cm and about 1 mS/cm, and dielectric constant, and the range is 1.8 to about 200.

36. The probe of claim 35, wherein the guard electrodes have an electric potential same as that of the signal electrode.

37. A probe for measuring electrical properties of a liquid, the probe comprising:
an electrode section comprising at least one inner cylindrical electrode and at least one outer cylindrical electrode;
a base portion upon which the at least one inner cylindrical electrode is mounted, the base portion having a first tapering section, and each at least one outer cylindrical electrode having a corresponding second tapering section configured such that the first and second tapering sections engage with each other to maintain precise concentricity between the at least one inner cylindrical electrode and the at least one outer cylindrical electrode;
two cylindrical guard electrodes respectively disposed adjacent an end of the inner signal electrode and electrically isolated from the signal electrode wherein the guard electrodes are configured to cause electric field lines between the outer cylinder electrode and the inner signal electrode to remain uniform over substantially an entire length of the inner signal electrode and reduce electric field fringing at the edges of the signal electrode, such that a cell constant change of the probe is negligible with respect to a range of the electrical properties of the liquid, whereby the electrical properties comprise liquid conductivity, and the range is between about 1 fS/cm and about 1 mS/cm, and dielectric constant, and the range is 1.8 to about 200; and
a fastener configured to hold the first and second tapering sections in a contacting relationship.

38. A probe according to claim 37, wherein the fastener comprises threads on the electrode section and the base portion.

39. A method of measuring an electrical property a liquid comprising:
applying to a liquid sample a first imposed waveform of a wave-shape, said wave-shape being chosen to be optimum for the sample liquid; and
periodically changing the wave-shape to optimize the first imposed waveform in response to dynamically changing values of conductivity or dielectric constant of the sample liquid, the changes in wave-shape being based on measured or expected values of the conductivity or the dielectric constant, caused by environmental, chemical or biological conditions in the sample liquid to be measured.

40. The method of claim 39, wherein periodically changing the wave-shape comprises periodically changing the wave-shape within a time period ranging from about 10 milliseconds to about 15 seconds.

* * * * *